US00PP11777P2

(12) United States Plant Patent
Davidson et al.

(10) Patent No.: US PP11,777 P2
(45) Date of Patent: Feb. 13, 2001

(54) HYBRID ASH TREE NAMED 'NORTHERN GEM'

(75) Inventors: Campbell G. Davidson, Morden; Wilbert G. Ronald, Portage la Prairie, both of (CA)

(73) Assignee: Her Majesty the Queen in right of Canada, as represented by the Minister of Agriculture, Ottawa (CA)

( * ) Notice: Under 35 U.S.C. 154(b), the term of this patent shall be extended for 0 days.

(21) Appl. No.: 09/233,439

(22) Filed: Jan. 20, 1999

(51) Int. Cl.[7] ..... A01H 5/00
(52) U.S. Cl. ..... Plt./219
(58) Field of Search ..... Plt./219

(56) References Cited

PUBLICATIONS

Davidson, Campbell G. 'Northern Treasure' and 'Northern Gem' hybrid ash. Hortscience 34 (1): p151–152. Feb. 1999.*

* cited by examiner

*Primary Examiner*—Bruce R. Campell
*Assistant Examiner*—Wendy A. Baker
(74) *Attorney, Agent, or Firm*—Burns, Doane, Swecker & Mathis, L.L.P

(57) ABSTRACT

A new and distinct *Fraxinus nigra* Marsh.×*Fraxinus mandshurica* Rupr. hybrid ash cultivar is provided which exhibits a vigorous growth habit. An attractive oval to round-shaped tree form with an acute branching character is exhibited. The tree crown is almost as wide as tall when grown in an open setting. Dull green compound leaves are formed. The flowers are perfect, seed production is low, and no production of viable seeds has been observed to date. The tree hardiness is good. The new cultivar is particularly well suited for growing as a shade tree.

4 Drawing Sheets

SUMMARY OF THE INVENTION

The original hybrid ash tree of the present invention was created during the early 1970's at the Agriculture and Agri-Food Canada Morden Research Centre, Morden, Manitoba, Canada, through the use of controlled breeding program. The female parent (i.e., the seed parent) was a Black Ash (*Fraxinus nigra* Marsh.) obtained from a native population in eastern Manitoba, Canada. The male parent (i.e., the pollen parent) was *Faxinus mandshurica* Rupr. that was originally obtained from the United States Department of Agriculture at Beltsville, Md. in 1959. The hybridization resulted in the formation of a population which included several promising seedlings including the new cultivar of the present invention having characteristics intermediate the two parental species. This controlled breeding program is believed to be the first known report of a hybrid ash cultivar that was created through the successful hybridization of these two species. The resulting seedlings were planted in the nursery row and have been observed for a period of over fifteen years. The final selection of the new cultivar was made in 1989. A single plant of the new variety was observed. The new cultivar also has undergone additional testing at regional trials in western Canada.

It has been found that the new *Fraxinus nigra* Marsh.× *Fraxinus mandshurica* Rupr. ash tree of the present invention exhibits:

(a) A vigorous growth habit, (b) An oval to round-shaped tree form, (c) Dull green pinnately compound leaves, (d) Forms perfect flowers, (e) Exhibits good hardiness, and (f) Is particularly well suited for use as a shade tree.

The new cultivar of the present invention has been found to combine the hardiness of the *Fraxinus nigra* Marsh. female parent with the form of the *Fraxinus mandshurica* Rupr. male parent.

The new cultivar of the present invention has been asexually reproduced beginning in the late 1970's by budding and grafting onto local strains of Green Ash (*Fraxinus pennsylvanica* Marsh.) at Morden, Manitoba, Canada. Such propagation has demonstrated that the combination of characteristics described herein is stable and is successfully transmitted to succeeding generations. The propagation can be similarly conducted on Black Ash (*Fraxinus nigra*).

The same cross identified above also formed the 'Northern Treasure' cultivar which is the subject matter of our U.S. Plant patent application Ser. No. 09/233,440, filed concurrently herewith. The new cultivar of the present invention can be readily distinguished from the 'Northern Treasure' cultivar since the new cultivar of the present invention exhibits a different form which is oval to round-shaped. The crown of the 'Northern Treasure' cultivar is upright with an acute branching habit. Also, the new cultivar of the present invention may be slightly less hardy than the sister 'Northern Treasure' cultivar.

The new hybrid ash tree of the present invention initially was designated No. 8920 and subsequently has been named the 'Northern Gem' cultivar.

BRIEF DESCRIPTION OF THE PHOTOGRAPHS

The accompanying photographs show, as nearly true as it is reasonably possible to make the same in a color illustrations of this character a typical tree and foliage of the new cultivar. The tree was growing at the Agriculture and Agri-food Canada Morden Research Centre, Morden, Manitoba, Canada. The photographs were prepared during July. Such tree had been propagated by budding on a Green Ash (i.e., *Fraxinus pennsylvanica* Marsh.) rootstock during approximately 1978.

FIG. 1 illustrates the overall tree configuration of the new cultivar when grown in an open setting. The oval to round-shaped tree crown which is almost as wide as tall is apparent.

FIG. 2 illustrates for comparative purposes typical leaves of the Black Ash (*Fraxinus nigra*) Marsh.), the new cultivar of the present invention, and of *Fraxinus mandshurica* Rupr. On the left is shown the upper surface of a leaf of the Black Ash. On the right is shown the under surface of a leaf of *Fraxinus mandshurica* Rupr. At the center is shown the upper surface of a leaf of the new cultivar of the present invention. The dull green leaf appearance is apparent. The white blotches are the result of insect feeding and are not an inherent characteristic of the leaf.

DETAILED DESCRIPTION

Figure 1:
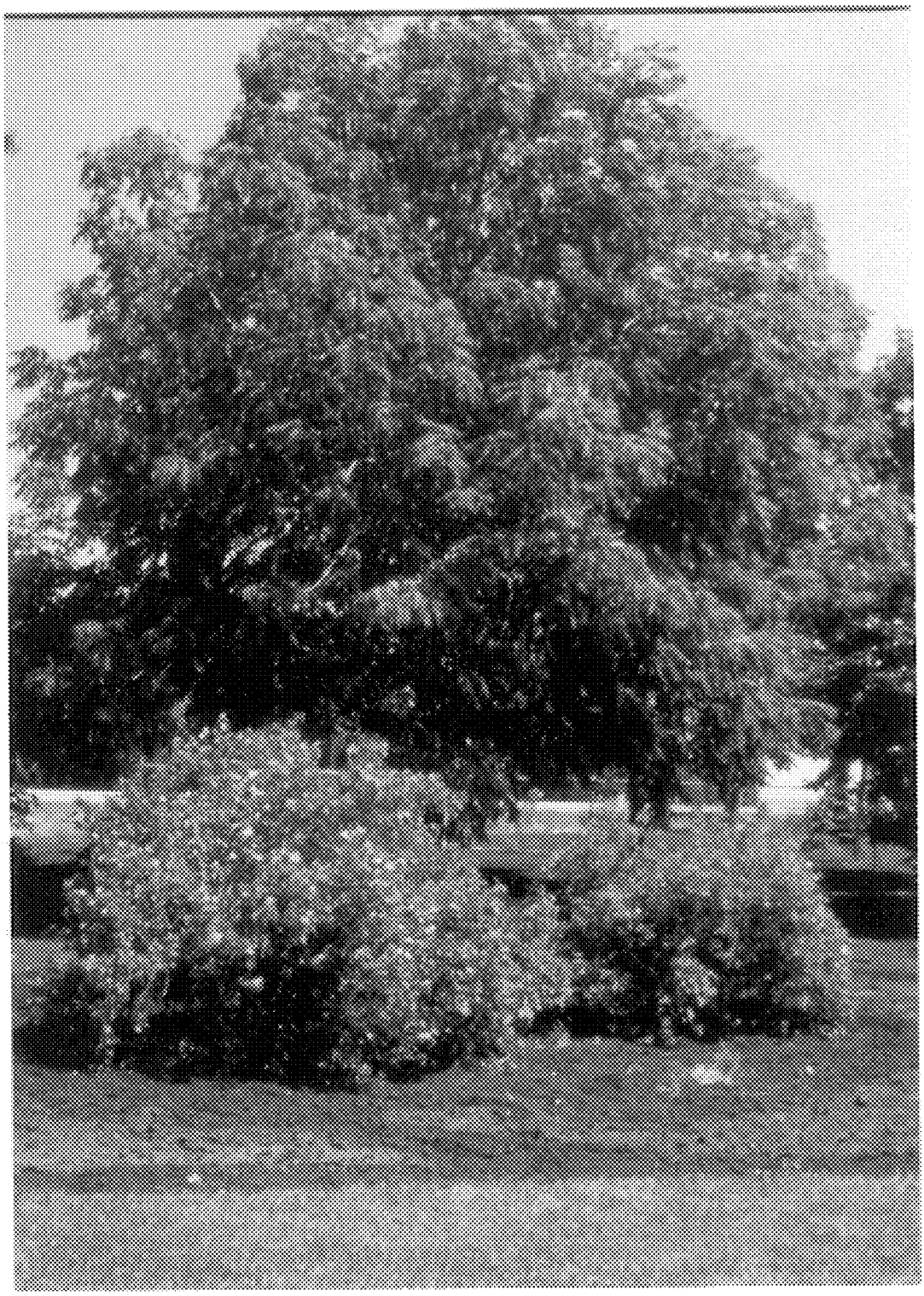
Figure 2:
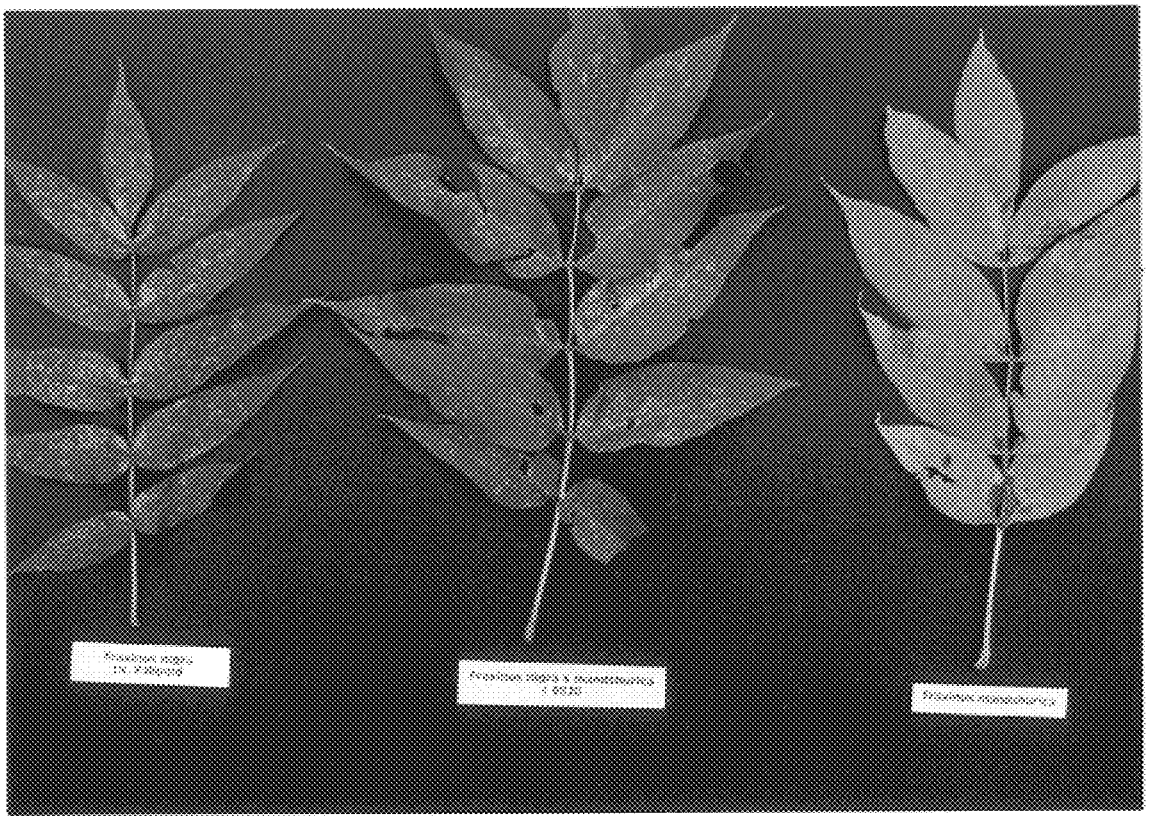
Figure 3:
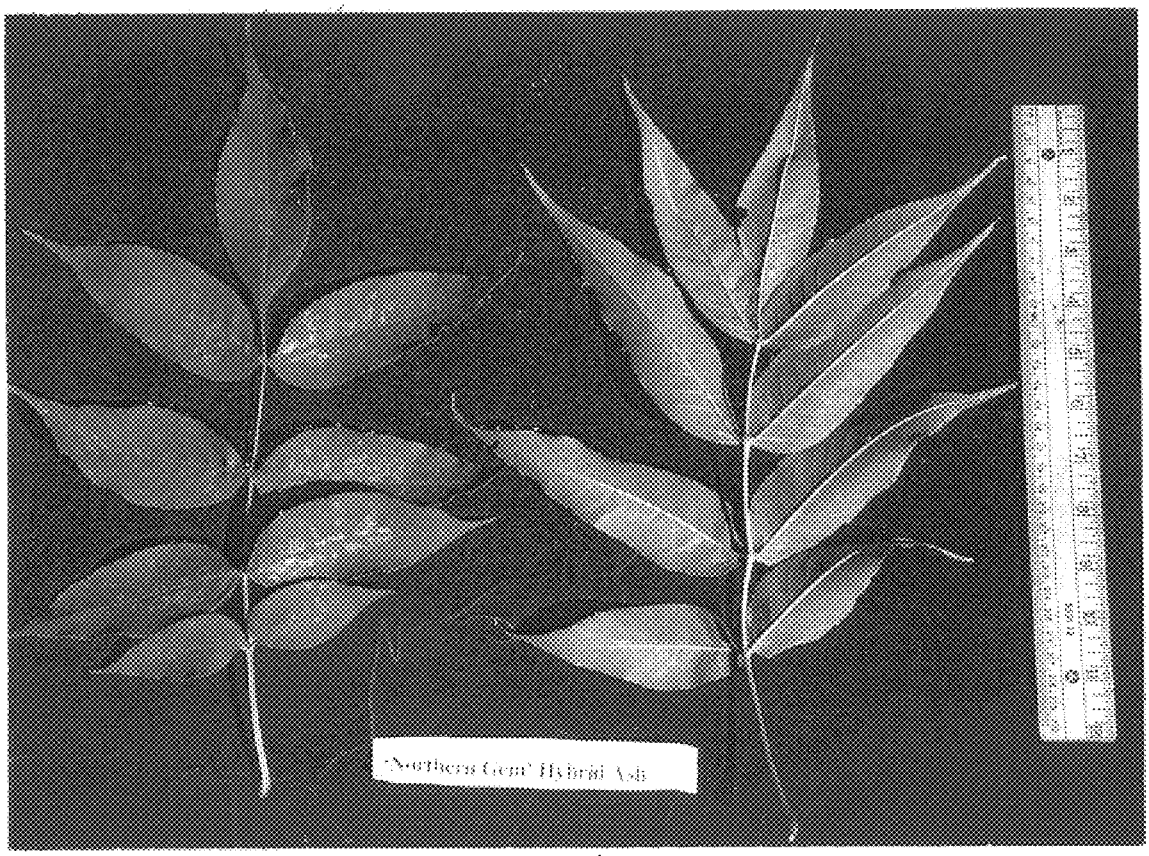
FIG. 3 illustrates typical leaves of the new cultivar with the under (abaxial) surface being shown at the right and the upper (adaxial) surface at the left.
Figure 4:
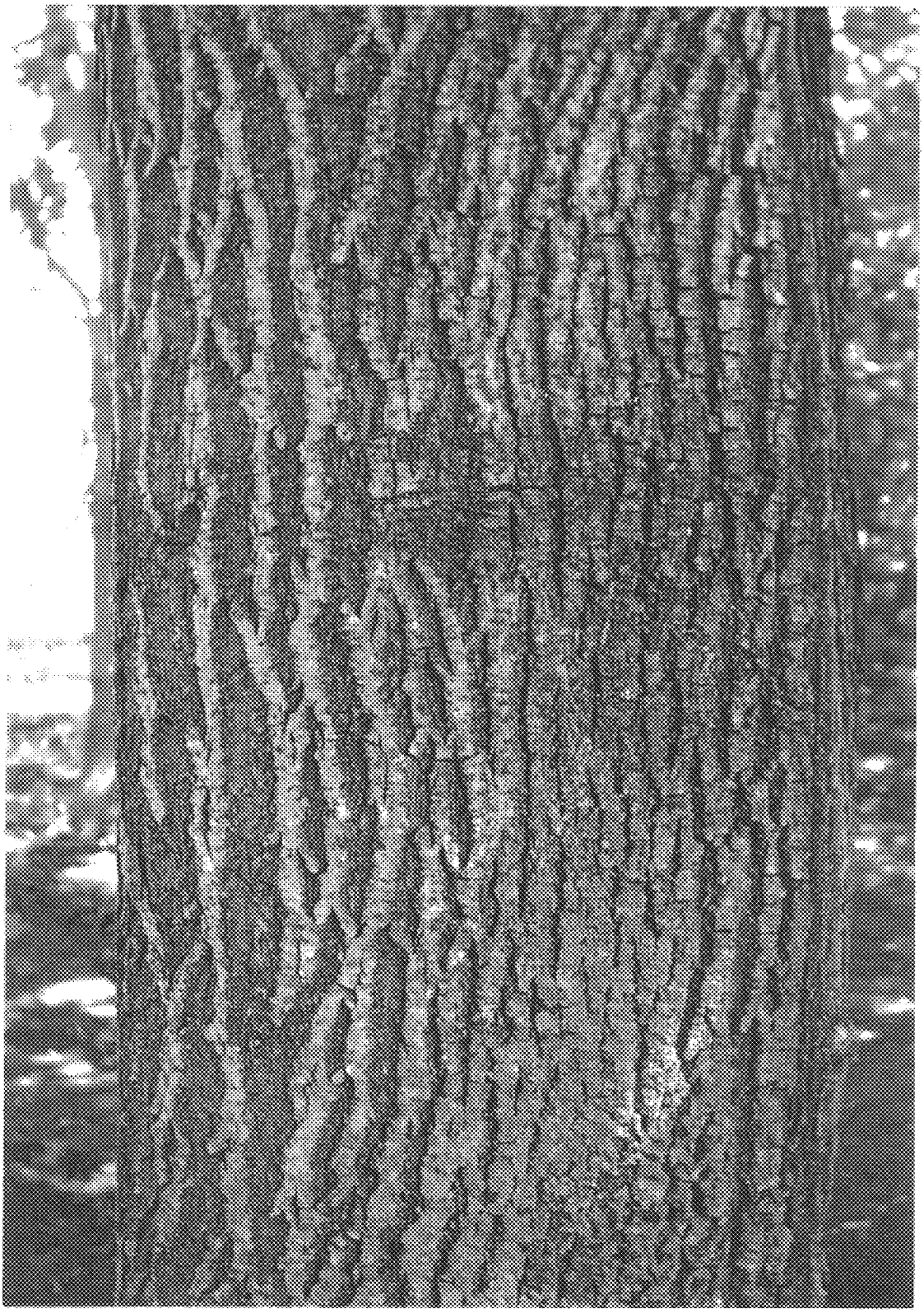
FIG. 4 illustrates typical deeply furrowed old mature bark of the new cultivar.

The chart used in the identification of colors is that of The Royal Horticultural Society (R.H.S. Colour Chart). Common terms are to be accorded their ordinary dictionary significance. The description is based upon the growing of trees at the Agriculture and Agri-Food Canada Morden Research Centre, Morden, Manitoba, Canada.

Botanical classification: *Fraxinus nigra* Marsh.×*Fraxinus mandshurica* Rupr., cv. 'Northern Gem'.

Plant:

*Growth habit.*—Oval to round-shaped when grown in an open setting. The mean branch divergence angle from the parent shoot commonly is approximately 69°. This can be compared to the upright growth habit of the sister 'Northern Treasure' cultivar, and the commonly observed mean branch divergence angle for the 'Northern Treasure' cultivar is more acute and approximately 50.7°.

*Size.*—A fifteen year-old tree commonly exhibits an average height of approximately 11.8 meters and an average canopy width at the widest point of approximately 8.7 meters. The trunk circumference at breast height commonly is approximately 98 cm. on average. This can be compared to an average height of approximately 12.2 meters, an average canopy width of at the widest point of approximately 5.9 meters, and an average trunk circumference of approximately 75 cm. for the sister 'Northern Treasure' cultivar.

*Bark.*—Grey-Brown Group 199A for current season, and Grey-Brown Group 199C for the previous season. This can be compared to Yellow-Green Group 152A for the current season and Grey-Brown Group 199B for the previous season for the 'Northern Treasure' cultivar. Old mature bark is deeply furrowed and varies in coloration from light grey to dark grey. Medium-aged bark along the trunk is light gray in coloration and not furrowed, but appears to be rough due to an abundance of brown-colored lenticels which protrude slightly from the bark surface. Young bark on new branches is light gray and smooth with small light-brown lenticels.

Foliage:

*Form.*—Pinnately compound.

*Number of leaflets.*—Commonly 9 to 11.

*Leaf configuration.*—Leaflets are sessile. Lateral leaflets have bases that are broadly cuneate with edges tapering at approximately a 45° angle. The terminal leaflet has a base that is narrowly cuneate with the edges tapering at approximately a 60° angle. The apex of the leaflets is narrowly acuminate with long slender tips. The leaflet margins are serrate.

*Leaf pubescence.*—Leaflets are densely pubescent/tomentose at the juncture where the sessile leaflet meets the petiole. The hairs are light brown in coloration and quite long and very tangled. Pubescence continues along the adaxial (i.e. upper) portion of the midrib of the leaf and on the underside of the leaf with lighter colored hairs The density of the hairs decreases from the base of the leaf to the apex. There is also a dense concentration of brown-colored hairs at the juncture where the lateral veins meet the midrib with hairs continuing for a short distance on the lateral veins. The upper and lower surfaces of the leaves are otherwise glabrous. The overall density of the hairs tends to be less than that of both parent species.

*Leaf length.*—Commonly approximately 35.6 cm. on average. This compares to an average length of approximately 32.9 cm. for the sister 'Northern Treasure' cultivar.

*Leaf width.*—Commonly approximately 29.5 cm. on average. This compares to an average width of 28.6 cm. for the sister 'Northern Treasure' cultivar.

*Leaflet length.*—Commonly approximately 15.7 cm. on average. This compares to an average length of 16.1 cm. for the sister 'Northern Treasure' cultivar.

*Leaflet width.*—Commonly approximately 5.2 cm. on average. This compares to an average width of 5.6 cm. for the sister 'Northern Treasure' cultivar.

*Leaf margins.*—Serrate.

*Length of terminal shoot.*—Mid-crown samples formed in 1994 and 1995 averaged 30.0 cm. and 25.6 cm. respectively. This compared to 32.0 cm. and 30.5 cm. for the sister 'Northern Treasure' cultivar.

*Diameter of terminal mid-shoot.*—6.4 cm. on average during the 1995 season. This compared to an average of 6.9 cm. for the sister 'Northern Treasure' cultivar.

*Diameter of lateral mid-shoot.*—5 cm. on average during the 1995 season. This compared to an average of 7.1 cm. for the sister 'Northern Treasure' cultivar.

*Leaf coloration.*—Dull green during the summer which is Green Group 137A on the upper surface and Yellow-Green Group 147B on the under surface. The fall coloration is yellow-orange (Yellow-Orange Group 20C) on the upper surface and Greyed-Yellow Group 162C on the under surface. In comparison the summer leaf coloration of the sister 'Northern Treasure' cultivar is shiny Yellow-Green Group 147A on the upper surface and Green Group 137C on the under surface. Also, the fall coloration of the 'Northern Treasure' cultivar is pale yellow-orange (Yellow-Orange Group 16C) on the upper surface and under surfaces.

*Length of terminal bud.*—Approximately 4.4 mm. on average. This compares to an average length of 5.6 mm. for the sister 'Northern Treasure' cultivar.

*Width of terminal bud.*—Approximately 4.6 mm. on average. This compares to an average width of 5.4 mm. for the sister 'Northern Treasure' cultivar.

*Color of terminal bud.*—Brown Group 200A for both the present cultivar and the sister 'Northern Treasure' cultivar.

*Length of lateral bud.*—Approximately 1.9 mm. on average. This compares to an average width of 2.6 mm. for the sister 'Northern Treasure' cultivar.

*Width of lateral bud.*—Approximately 2.8 mm. on average. This compares to an average width of 4 mm. for the sister 'Northern Treasure' cultivar.

*Color of lateral bud.*—Brown Group 200A for both the present cultivar and the sister 'Northern Treasure' cultivar.

*Inflorescence:*

*Nature.*—Plants are monoecious with imperfect flowers in an inflorescence (i.e. an inflorescence that has both male and female flowers).

*Seed production.*—During the flowering and fruit ripening process, immature seeds typical of *Fraxinus niger* sometimes have been observed. Such seeds commonly are less than 1 inch in length and are aborted early in their development. The aborted seeds do not remain attached to the inflorescence. The presence of these seeds is not a detriment since the seeds do not germinate. The tree is functionally sterile even though in the early part of the growing season seeds sometimes are visible. Immature seeds have been gathered in an attempt to germinate them. All attempts at germination have failed to date.

*Fertility.*—No viable seeds have been observed to date.

Development:

*Vegetation.*—Vigorous. Early growth in nursery environments is very rapid and often exceeds two meters in height at the end of the second year.

*Insect resistance.*—No damage by flower gall insects has been observed to date.

*Hardiness.*—Good. The new cultivar is well suited for growing in the northern Great Plains. In controlled laboratory freezing assessments the new cultivar had good acclimation rates and low temperature tolerance. Some tip dieback in nursery plants has been observed on occasion when grown in U.S.D.A. Zone No. 3.

We claim:

1. A new and distinct *Fraxinus nigra* Marsh.×*Fraxinus mandshurica* Rupr. ash tree which exhibits the following combination of characteristics:

(a) A vigorous growth habit, (b) An oval to round-shaped tree form, (c) Dull green pinnately compound leaves, (d) Forms perfect flowers, (e) Exhibits good hardiness, and (f) Is particularly well suited for use as a shade tree; substantially as illustrated and described.

* * * * *